United States Patent [19]

Kayser

[11] Patent Number: 4,604,489
[45] Date of Patent: Aug. 5, 1986

[54] RECRYSTALLIZATION OF HEXANITROSTILBENE FROM DIMETHYLSULFOXIDE AND METHANOL

[75] Inventor: Eleonore G. Kayser, Baltimore, Md.

[73] Assignee: The United States of America as represented by the Secretary of the Navy, Washington, D.C.

[21] Appl. No.: 602,577

[22] Filed: Apr. 20, 1984

[51] Int. Cl.$^4$ .............................................. C07C 79/10
[52] U.S. Cl. .................................. 568/931; 568/930
[58] Field of Search ................ 568/930, 931; 260/707; 422/245–252

[56] References Cited

U.S. PATENT DOCUMENTS

| | | | |
|---|---|---|---|
| 2,288,667 | 7/1942 | Allen et al. | 422/245 |
| 3,505,413 | 4/1970 | Shipp | 260/645 |
| 3,600,139 | 8/1971 | Hedrick | 422/252 |
| 3,941,853 | 3/1976 | Shipp et al. | 568/931 |
| 4,221,745 | 9/1980 | Gilbert | 568/931 |
| 4,221,746 | 9/1980 | Gilbert | 568/931 |
| 4,234,614 | 1/1981 | Gilbert | 568/931 |
| 4,260,837 | 4/1981 | Dacons | 568/931 |
| 4,268,696 | 5/1981 | Sollot et al. | 568/931 |
| 4,270,012 | 5/1981 | Gilbert | 568/931 |

*Primary Examiner*—John F. Terapane
*Assistant Examiner*—T. J. Wallen
*Attorney, Agent, or Firm*—Kenneth E. Walden; Roger D. Johnson

[57] ABSTRACT

The production of 2,2′,4,4′,6,6′-hexanitrostilbene-II (HNS-II) having finely divided particles of uniform size by dissolving HNS-II in hot dimethylsulfoxide and then injecting the hot solution through a small orifice into methanol at a temperature of from −50° C. to −80° C.

3 Claims, No Drawings

United States Patent 4,604,489

RECRYSTALLIZATION OF HEXANITROSTILBENE FROM DIMETHYLSULFOXIDE AND METHANOL

BACKGROUND OF THE INVENTION

This invention relates to aromatic compounds and more particularly to aromatic compounds containing nitro groups.

2,2',4,4',6,6'-hexanitrostilbene (HNS) is an explosive which is used in explosive actuating devices, detonating cords, flexible shape charges, etc. The HNS-I which is produced by conventional methods is crude and contains substantial amounts of hexanitrobibenzyl as an impurity. As a result, crude HNS-I has poorer thermal stability properties than HNS-II. Washing the crude produce with solvent only removes the surface contaminents; impurities which have cocrystallized or occluded with the product HNS-I are not removed. Another approach is to digest the crude HNS-I by heating it in organic solvents; however, crystal growth occurs during this process and a wide particle size distribution results. Yet another method of purification is to dissolve the crude HNS-I in hot fuming nitric acid and then allow the solution to slowly cool to room temperature. This method produces a purer larger particle HSN-II. U.S. Pat. No. 4,260,837 discloses a method of producing purer small particle HNS-I by dissolving crude HNS-I in hot fuming nitric acid and then drowning the HNS-nitric acid solution in water. Unfortunately, these last two methods produce HNS crystals which are slightly contaminated with nitric acid and which therefore have lower thermal stabilities than is necessary for many applications.

SUMMARY OF THE INVENTION

Accordingly, an object of this invention is to provide a new method of recrystallizing 2,2',4,4',6,6'-hexanitrostilbene-II.

Another object of this invention is to provide high purity, finely divided 2,2',4,4',6,6'-hexanitrostilbene-II.

A further object of this invention is to provide 2,2',4,4',6,6'-hexanitrostilbene having a high degree of thermal stability.

Yet another object of this invention is to provide 2,2',4,4',6,6'-hexanitrostilbene having a uniform particle size.

A still further object of this invention is to provide 2,2',4,4',6,6'-hexanitrostilbene in a form which is suitable for use in detonation cords, flexible shape charges, and other flexible explosive devices in a high temperature environment.

These and other objects of this invention are accomplished by providing a process for producing finely divided 2,2',4,4',6,6'-hexanitrostilbene-II (HNS-II) comprising:

(1) dissolving large particle 2,2',4,4',6,6'-hexanitrostilbene-II in hot dimethylsulfoxide (DMSO);

(2) injecting the hot dimethylsulfoxide solution through an opening of 0.70 mm or less in diameter into methanol which is kept at a temperature of from $-50°$ C. to $-80°$ C.; and (3) isolating the finely divided particles of 2,2',4,4',6,6'-hexanitrostilbene-II which are produced in Step (2).

DETAILED DESCRIPTION OF THE PREFERRED EMBODIMENTS

As stated in the background of the invention, recrystallization of crude 2,2',4,4',6,6'-hexanitrostilbene-I (HNS-I) by dissolving it in hot fuming nitric acid and then allowing the acid mixture to cool to room temperature produces large particles of HNS-II. In that process the impurity hexanitrobibenzyl is removed but traces of $HNO_3$ are introduced into the HNS. The presence of $HNO_3$ reduces the thermal stability of the HNS to an unacceptable level at high temperatures.

The present process produces small crystals of HNS-II which do not contain $HNO_3$. Because the particles are very small, the occlusion of other solvents and impurities is kept to a minimum. The thermal stability of the HNS-II is therefore higher.

In this process large particle HNS-II is dissolved in hot dimethylsulfoxide (DMSO). The hot HNS/DMSO solution is then injected in a fine stream into methanol which is kept at a temperature of from $-50°$ C. to $-80°$ C., but preferably from $-65°$ C. to $-75°$ C. The fine stream of HNS/DMSO is created by injecting the solution through an opening (e.g., jet or tube) having an internal diameter of 0.70 mm or less and preferably of 0.40 mm or less. The lower limit on the diameter of the tube is determined by practical considerations such as what size tubing is available and at what rate the crystals are to be produced.

Another variation of this invention is to blow a stream of atomized HNS-II/DMSO solution in an inert gas (argon, helium, nitrogen, etc.) into the methanol. In this manner much smaller purer crystals of HNS-II will be produced.

The product crystals of HNS-II are then collected and washed with methanol (or a similar solvent). Finally, the HNS-II is dried at 70° C. under vacuum.

The general nature of the invention having been set forth, the following example is presented as specific example thereof. It will be understood that the invention is not limited to this specific example but is susceptible to various modifications that will be recognized by one of ordinary skill in the art.

EXAMPLE

Approximately 400 to 500 milligrams of large particle size 2,2',4,4',6,6'-hexanitrostilbene-II (HNS-II) was dissolved in 10 ml of hot dimethylsufoxide (DMSO). This HNS-II/DMSO solution was quickly injected through a ⅜27 needle into 150 ml of methanol cooled to dry-ice-/acetone temperature ($-70°$ C.). The HNS-II/D-MSO/methanol solution was filtered and the resulting solid was washed three times with approximately 100 ml of methanol and filtered. The solid was dried under vacuum at approximately 100° C. for several hours.

This process increased the surface area of the HNS-II from 2,076 $cm^2/cm^3$ to 147,012 $cm^2/cm^3$.

Obviously, numerous modifications and variations of the present invention are possible in light of the above teachings. It is therefore to be understood that within the scope of the appended claims the invention may be practiced otherwise then as specifically described herein.

I claim:

1. A process for producing finely divided 2,2',4,4',6,6'-hexanitrostilbene-II (HNS-II) of uniform particle size comprising:

(1) dissolving conventional large particle 2,2′,4,4′,6,6′-hexanitrostilbene-II in hot dimethylsulfoxide (DMSO), wherein the large particle HNS-II had been produced by digestion of crude 2,2′,4,4′,6,6′-hexanitrostilbene-I in an organic solvent;

(2) injecting the hot dimethylsulfoxide solution through an opening of 0.70 mm or less in diameter into methanol which is kept at a temperature of from −50° C. to −80° C.; and (3) isolating the finely divided particles of 2,2′,4,4′,6,6′-hexanitrostilbene-II which are produced in step (2).

2. The process of claim 1 wherein the temperature of the methanol in step (2) is kept at a temperature of from −65° C. to −75° C.

3. The process of claim 1 wherein the opening in step (2) is 0.40 mm or less in sized.

* * * * *